(12) United States Patent  
Schuster et al.

(10) Patent No.: US 7,301,621 B2  
(45) Date of Patent: *Nov. 27, 2007

(54) METHOD AND DEVICE FOR NON-DESTRUCTIVE ANALYSIS OF PERFORATIONS IN A MATERIAL

(75) Inventors: Jeffrey A. Schuster, Oakland, CA (US); Sudarsan Srinivasan, Fremont, CA (US); Thor Miller Wilbanks, Berkeley, CA (US)

(73) Assignee: Aradigm Corporation, Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/463,412

(22) Filed: Aug. 9, 2006

(65) Prior Publication Data

US 2007/0019187 A1    Jan. 25, 2007

Related U.S. Application Data

(63) Continuation of application No. 10/642,436, filed on Aug. 14, 2003, now Pat. No. 7,148,960, which is a continuation-in-part of application No. 09/330,254, filed on Jun. 10, 1999, now Pat. No. 6,624,885.

(51) Int. Cl.  
*G01N 21/00* (2006.01)

(52) U.S. Cl. .................................. 356/237.6

(58) Field of Classification Search ...... None  
See application file for complete search history.

(56) References Cited

U.S. PATENT DOCUMENTS

| | | |
|---|---|---|
| 3,711,205 A | 1/1973 | Tulk et al. |
| 3,806,252 A | 4/1974 | Harris et al. |
| 4,596,037 A | 6/1986 | Bouchard et al. |
| 4,647,208 A | 3/1987 | Bieman |
| 4,930,889 A | 6/1990 | Van Donselaar et al. |
| 5,026,964 A | 6/1991 | Somers et al. |
| 5,063,280 A | 11/1991 | Inagawa et al. |
| 5,497,764 A | 3/1996 | Ritson et al. |
| 5,528,359 A | 6/1996 | Taguchi |
| 5,544,646 A | 8/1996 | Lloyd et al. |
| 5,660,166 A | 8/1997 | Lloyd et al. |
| 5,709,202 A | 1/1998 | Lloyd et al. |
| 5,718,222 A | 2/1998 | Lloyd et al. |
| 5,745,168 A | 4/1998 | Ninomiya |
| 5,823,178 A | 10/1998 | Lloyd et al. |
| 5,829,435 A | 11/1998 | Rubsamen et al. |
| 6,140,604 A | 10/2000 | Somers et al. |
| 6,196,218 B1 * | 3/2001 | Voges .................... 128/200.14 |
| 6,441,340 B1 | 8/2002 | Variano-Marston |
| 6,624,885 B1 | 9/2003 | Pon et al. |
| 7,148,960 B2 * | 12/2006 | Schuster et al. ......... 356/237.6 |

* cited by examiner

*Primary Examiner*—Michael P. Stafira  
(74) *Attorney, Agent, or Firm*—Karl Bozicevic; Bozicevic, Field & Francis LLP

(57) ABSTRACT

Method for fabricating and inspecting small holes in a material are disclosed. The method includes directing light onto the material and through the holes formed in the material, and then collecting the light passing through the holes in the material onto a detector. The methods further include analyzing the light for properties of the holes, and modifying the process based these detected properties.

13 Claims, 4 Drawing Sheets

METHOD AND DEVICE FOR NON-DESTRUCTIVE ANALYSIS OF PERFORATIONS IN A MATERIAL

FIELD OF THE INVENTION

The invention relates generally to methods of non-destructive analysis. More particularly, the invention relates to a method and device for quickly and non-destructively analyzing an array of small holes precisely placed in a material such as a thin film.

BACKGROUND OF THE INVENTION

In different areas of technology it is desirable to make use of a thin sheet of material which has an array of regularly spaced, very small holes therein. For example, such might be used in the manufacture of various electronic components. Thin sheets which have one or more holes in them could also be used in the formation of components used in ink jet printers or fuel injectors. A more direct application of such a pore array is as a filter. The pore size and pore density could be adjusted to wide range of filter applications. Alternatively, liquid formulations containing a drug could be moved through such a porous member to create an aerosol for inhalation.

One of the gentlest and most acceptable methods of administering an agent to a patient is via aerosol. Aerosol therapy can be accomplished by aerosolization of a formulation (e.g., a drug formulation or diagnostic agent formulation) and administration to the patient, for example via inhalation. The aerosol can be used to treat lung tissue locally and/or be absorbed into the circulatory system to deliver the drug systemically. Where the formulation contains a diagnostic agent, the formulation can be used for diagnosis of, for example, conditions and diseases associated with pulmonary dysfunction.

In general, aerosolized particles for respiratory delivery must have a diameter of 12 microns or less. However, the preferred particle size varies with the site targeted (e.g., delivery targeted to the bronchi, bronchia, bronchioles, alveoli, or circulatory system). For example, topical lung treatment can be accomplished with particles having a diameter in the range of 1.0 to 12.0 microns. Effective systemic treatment requires particles having a smaller diameter, generally in the range of 0.5 to 6.0 microns, while effective ocular treatment is adequate with particles having a diameter of 15 microns or greater, generally in the range of 15-100 microns.

U.S. Pat. Nos. 5,544,646, 5,709,202, 5,497,763, 5,544,646, 5,718,222, 5,660,166, 5,823,178 and 5,829,435 describe devices and methods useful in the generation of aerosols suitable for drug delivery. These devices generate fine, uniform aerosols by passing a formulation through a nozzle array having micron-scale pores as may be formed, for example, by LASER ablation.

Pore arrays having such small features are difficult and costly to manufacture. Additionally, the pores must be of high quality and uniformity where they are to be used (1) in manufacturing electronic components; (2) in filter materials; (3) in ink jet printers; (4) in fuel injectors; and (5) to create aerosols for delivering therapeutic agents to patients in order to insure that the patients consistently receive the therapeutically required dose. Consequently, there is a need for a fabrication method and an inspection method which can rapidly manufacture and analyze porous samples of small dimensions to determine various parameters including pore size and pore density, and with the ability to adjust such parameters to produce a pore array having high quality and uniform pores.

SUMMARY OF THE INVENTION

Thin films having small holes therein (pore arrays) are inspected or non-destructively analyzed by (1) shining a light through the pores of the sheet (2) detecting light which has passed through the pores and (3) analyzing the detected light in a manner which makes it possible to quickly determine whether the sheet should "pass" inspection based on criteria such as pore size and pore density. The device used in the inspection must include (1) a light source (2) a light detector and (3) a means for analyzing the detected light. Other components may be and generally are present such as light filters and lens for improving the overall accuracy of the system and a means for moving sheets into and out of position to improve the overall efficiency of the system.

The inspection system of the invention can carry out non-destructive inspection for the presence of microscopic pores within a thin film and determine the characteristics of the pore array including the pore size and shape, pore density and overall acceptability of the pore array. The system includes the ability to detect the light transmitted through the holes within the sheet and utilize the detected light information to develop a relationship between the level of light and the existence, location, size and shape of the hole, i.e., light levels detected from each hole-feature can be related to the individual size or shape of the hole. Further, the light levels from an entire array of pores within a sheet can be related to the collective average size and/or shapes of the holes. If the pores within the sheet do not meet a required criteria an alarm can be triggered at a given threshold level indicating that the pore array being tested does not have an adequate number of holes having the desired size and/or shape. Such an evaluation is preferably made on an overall reading of the pore array. More specifically, light is shown on the pore array and allowed to move through the holes to a detector. If the detector does not detect a desired quantity of light, either an insufficient number of holes has been formed or the holes are of insufficient size or shape or some combination thereof. Further, if too much light is detected, either the holes are too large, have an undesired shape, or there are too many holes present in the sheet. Falling above or below the detected amount of light triggers an alarm which causes the pore array being inspected to be rejected.

The system is capable of being used in connection with a variety of different pore arrays. The pores can have different sizes or shapes and can be present on the sheet in a variety of different patterns and pore densities. These different sheets with different patterns and pore sizes can be detected using the same charge-coupled light detector element and processed using the same microprocessor unit. If necessary the system can utilize a variety of different components including mirrors, rhomboids, wedges, or combinations thereof in order to obtain the desired results with a given pore array of the same basic components of the inspection system.

The inspection system of the invention can be used to check all of the pore arrays produced by a given production system or used to spot-check a certain percentage amount of those pore arrays. Further, the system can be integrated into a production system so that sheets are inspected at a given point before being used in an assembly process to produce a component which includes a pore array. When utilized in this manner the pore array need not be removed from the system for inspection purposes. Light transmitted through the pores of the sheet can be detected and used as a trigger to accept or reject the pore array for further use in the manufacturing process.

The inspection system of the invention may be a part of or used with a fabrication system for forming the holes that constitute pore arrays. The fabrication system includes an energy source and an energy transporter for directing the energy from the energy source to one or more locations on the sheet to be drilled. The energy source, such as a focused LASER light, is used to create the pores in the sheet. The pores may be formed successively (one pore at a time) or simultaneously (multiple pores at once) or any combination thereof, i.e., fabricating a pore array by sequentially fabricating subsets of the array that consist of multiple holes. The same light which is used to form the pores may also be used to carry out the inspection, as discussed above, in real time. As the LASER drills through the sheet, light from the LASER (or possibly another source) begins to impact the detector. More specifically, the LASER light used in order to create the holes can be detected by the detector and used to determine if the holes have been made, made in sufficient size, made with the correct shape, whether the pore density is sufficient, or any other property of the pore array. The light may be transmitted through one hole at a time, multiple holes in aggregate, or multiple holes individually.

Further, the present invention may further include an energy feedback or control mechanism for controlling the amount or intensity of energy being delivered to the sheet and/or for controlling the direction or angle at which the energy is being delivered to the pore array. The feedback control mechanism utilizes the output of the detector to determine whether some property of the light detected has reached a threshold level, e.g. a minimum or maximum energy level indicative of the size, shape or number of holes that have been formed within the sheet. For example, if the LASER light used in making the holes in the sheet is detected, the detection of a certain amount, e.g., a threshold level, of light can signal that the holes are sufficiently large or have reached the desired pore size thereby signaling that the LASER light should be discontinued in order to prevent the hole from being made too large. Alternatively, the intensity, amount, pulse frequency, pulse duration, polarization, wavelength, or any other characteristic of the light may be modified based on measured parameters of the light transmitted through a hole or multiple holes. The LASER light may be modified to produce a different set of holes than the ones that are transmitting the power to be analyzed, e.g., the power to an array of holes may be modified based on the light transmitted through a sub-set of the holes. In this manner it is possible to repeatedly and accurately produce pores of a very small size in a sheet. In accordance with this method the detection/inspection components of the invention are integrated with the controlled LASER. Thus, by this method of the invention the analysis and manufacture are truly carried out simultaneously and carried out in a manner which they complement each other. The method preferably can be carried out to simultaneously drill and analyze two, three or a plurality of holes at the same time.

The present invention rapidly inspects samples for holes or through features as small as the micron and sub-micron level. This method can be used to inspect previously manufactured samples, or can be integrated into the manufacturing process in order to allow for concurrent production and inspection of samples containing such features. In one aspect of the invention, an imaging lens is used to reduce the size of the image which must be inspected, allowing for more rapid inspection and requiring a smaller CCD detector and shorter analysis time of the smaller image.

An aspect of the invention is a method of analyzing a pore array which involves directing light onto a pore array, detecting light passing through pores of the sheet and then analyzing the detected light in a manner which determines if the pores of the sheet meet desired criteria.

Another aspect of the invention is a method of analyzing a pore array by directing light onto the pore array, detecting light reflecting off of the sheet and analyzing the reflected light in a manner such that the analysis determines if pores of the sheet meet a desired criteria.

Another aspect of the invention is an analysis system which includes a means for directing light onto a pore array, a means for detecting light which is reflected off of and/or light which passes through pores of the sheet and a means for analyzing either the reflected light and/or the light passing through pores of the sheet so as to determine if pores of the sheet meet a desired criteria.

A preferred aspect of the invention includes a means for moving one pore array after another into position for analysis or moving the system relative to the sheets in order to continuously analyze one sheet after another.

In another aspect of the invention comprises a film, e.g., a polyimide film containing LASER-ablated pores which has been inspected to determine the number and size of the pores.

In still another aspect of the invention, the light source employed produces ultraviolet light which is selectively transmitted through the features in the inspected sample.

In still another aspect of the invention, the light used to fabricated the pore or pores is detected, and some parameter or parameters of the light are modified based on some parameter or parameters that are detected.

In an additional aspect of the invention, a method of producing an aerosolization container comprising an aerosolization nozzle passing the inspection method is provided.

In a further aspect of the invention, a method of producing an aerosolization device comprising such a container is also provided.

An advantage of the invention is that pore arrays can be quickly, accurately and efficiently inspected. Another advantage of the invention is that the fabricated pore sizes and shapes can be very tightly controlled, and smaller features can be achieved, leading to a better performing final product.

A feature of the invention is that different types of light sources can be used and different types of filters can be used and positioned differently relative to the sheet being inspected.

Another feature of the invention is that the sheet may be moved relative to the light source and detector or the light source and/or detector may be moved relative to the sheet.

These and other aspects, objects, advantages and features of the present invention will become apparent to those skilled in the art upon reading this disclosure and reviewing the drawings forming a part hereof.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures:

FIG. 1 is a schematic drawing of a system of the present invention used to inspect samples for the size and number of holes passing through the sample.

Figure 1:
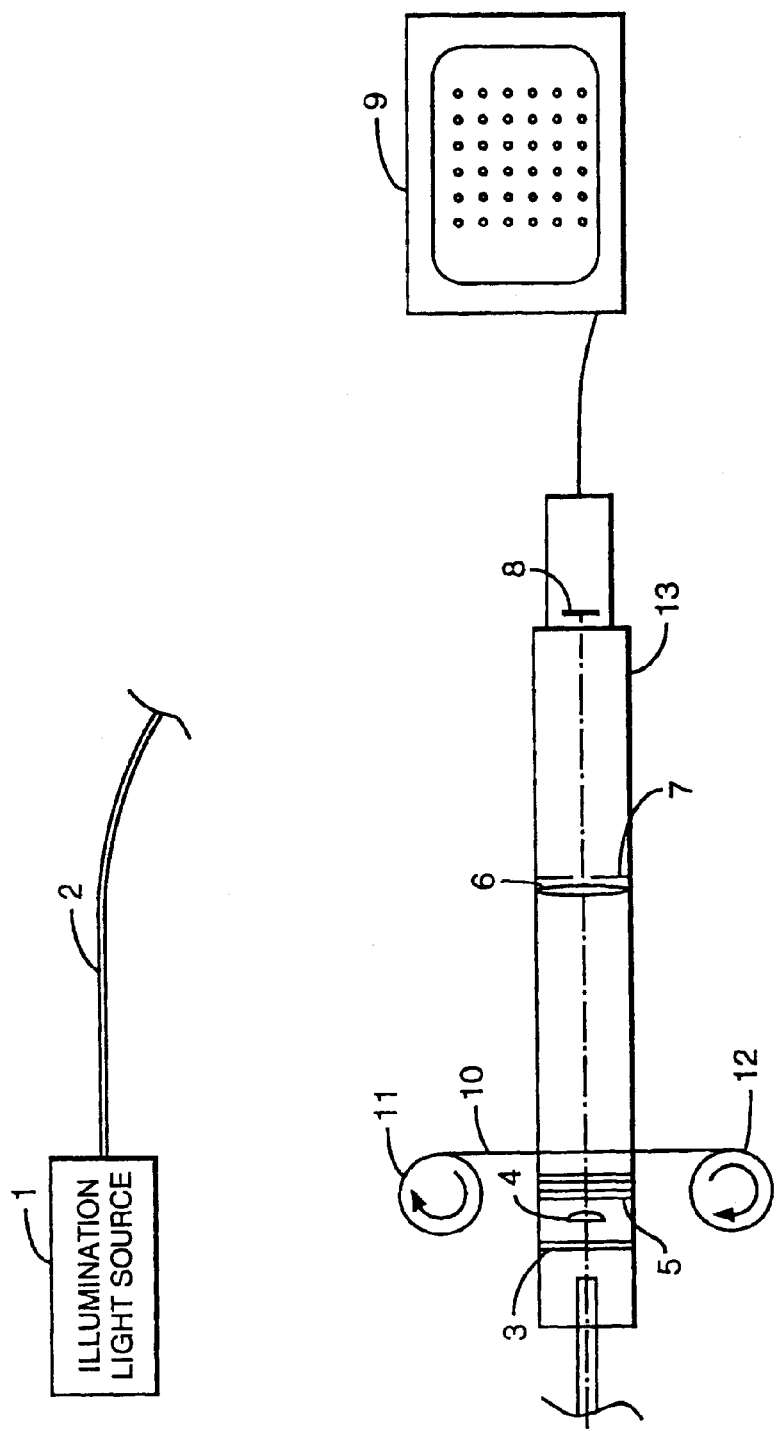
Figure 2:
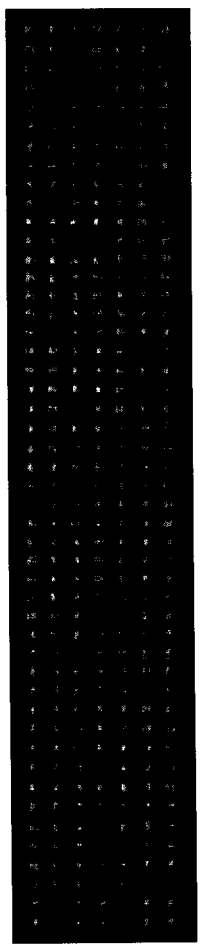
FIG. 2 shows optical images from samples which pass inspection following the inspection method of the present invention.
Figure 3:
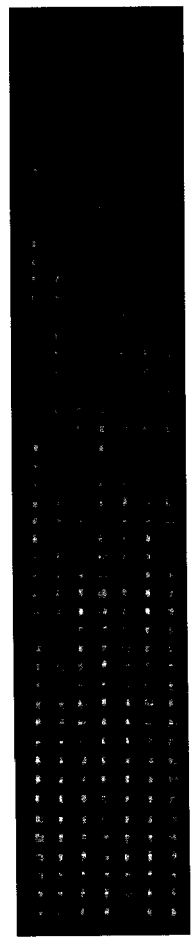
FIG. 3 shows optical images of samples which do not pass inspection from the inspection method of the present invention.
Figure 4:
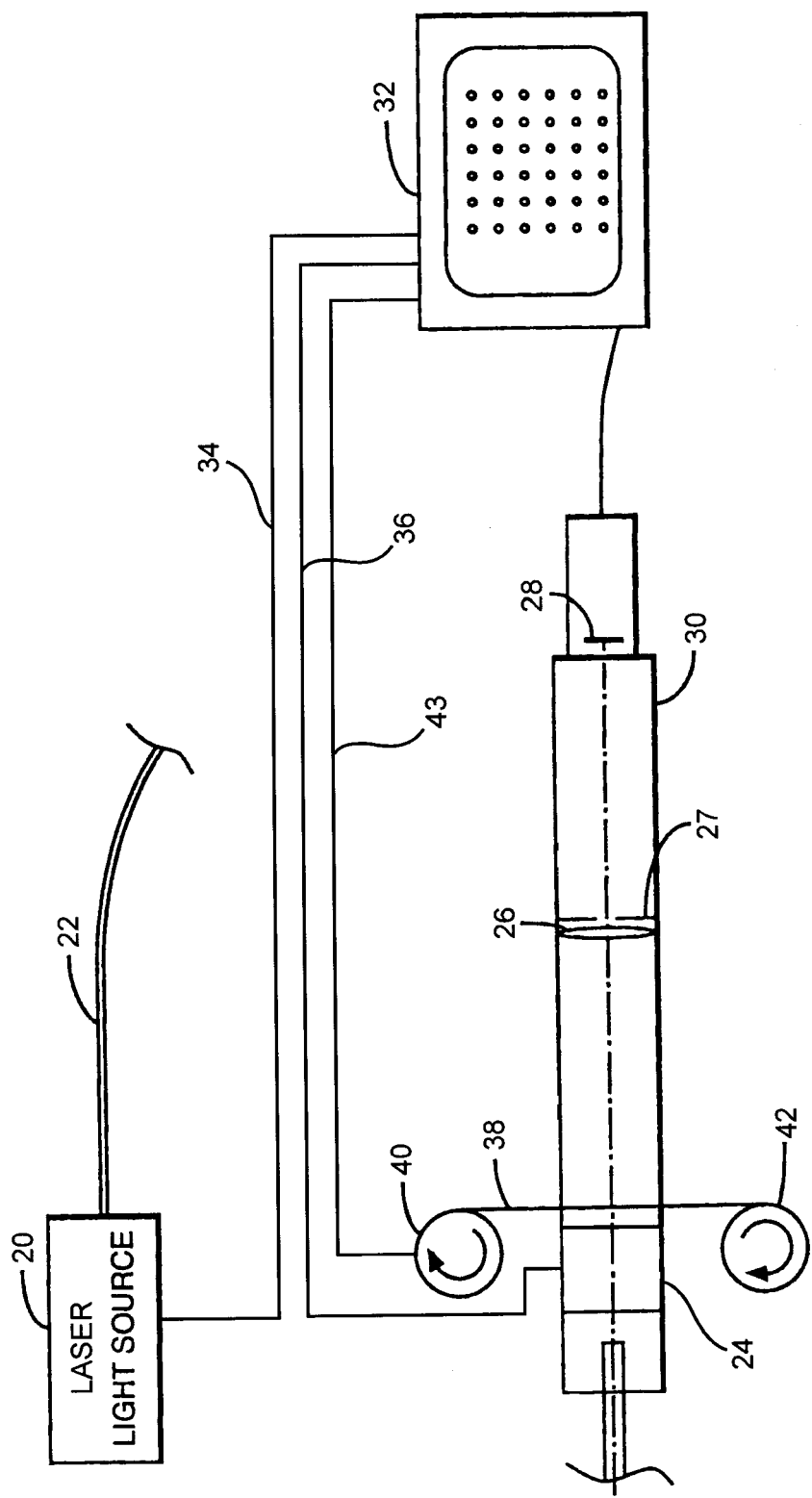
FIG. 4 is a schematic drawing of another system of the present invention used to form pores within a sheet and having a feedback control mechanism for controlling the size and number of pores to be formed.
Figure 5:
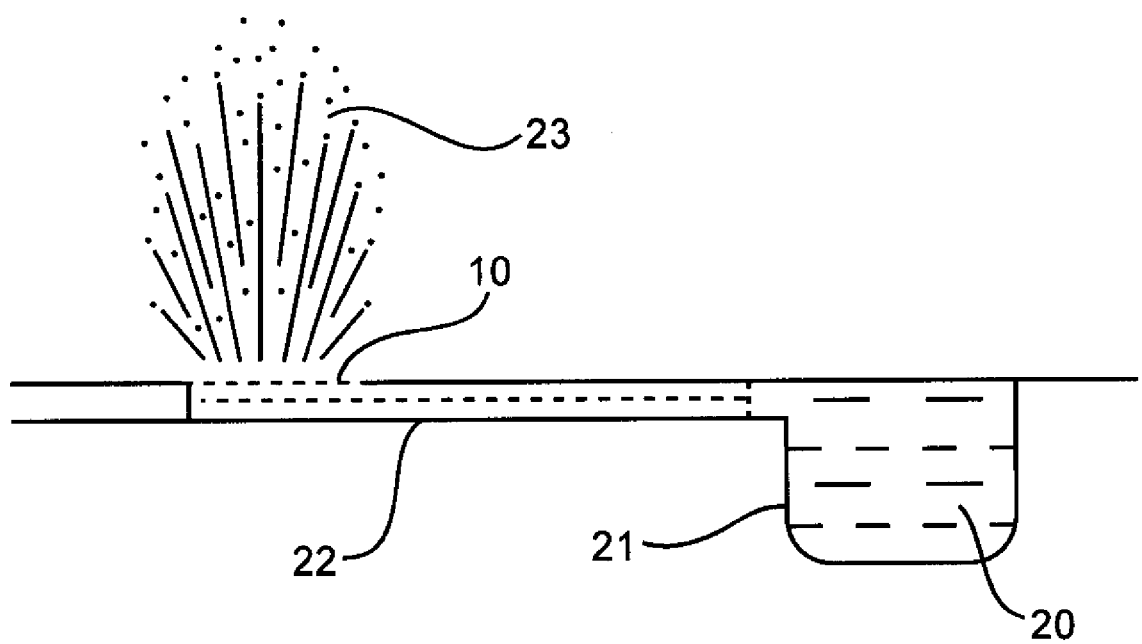
FIG. 5 is a schematic cross-sectional drawing of a formulation moving through the pores of a pore array to create an aerosol.

DESCRIPTION OF THE PREFERRED EMBODIMENTS

Before the present methods and systems of detecting and analyzing the holes are disclosed, it is to be understood that this invention is not limited to the particular methodology and devices described, as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an analyzing means" includes one or more of such means, and reference to "the method" or "the step" includes reference to equivalent steps and methods known to those skilled in the art, and so forth.

Where a range of values is provided, it is understood that each intervening value between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller range is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited.

The publications discussed above are provided solely for their disclosure prior to the filing date of the present application. Nothing herein is to be construed as an admission that the invention is not entitled to antedate such disclosure by virtue of prior invention.

Definitions

The term "porosity" is used herein to mean a percentage of an area of a surface area that is composed of open space, e.g., a pore, hole, channel or other opening, in a sheet, nozzle, filter or other material. The percent porosity is thus defined as the total area of open space divided by the area of the material, expressed as a percentage (multiplied by 100). High porosity (e.g., a porosity greater than about 50%) is associated (in applications where the pore array subsequently has liquid passed though it, e.g., aerosolization nozzles, fuel injectors, or filters) with high flow rates per unit area and low flow resistance. In general, the porosity of the pore array is less than about 10%, and can vary from about $10^{-5}$% to about 10%. Pore arrays of the invention may have any porosity without limitation. Further, a pore array may have any number of pores (including one), any pore density, any pore shape, or any pore size. For example, a sheet may have a single pore which can range considerably in size or have thousands of pores each of which could be the same or different in size and range considerably in size. In many applications the area of the material is not well defined, i.e., the pores may exist only in a small fraction of the sheet. In this case, the porosity will be taken to mean the porosity in the area defined by the existence of pores, and not of the total area of the sheet.

The term "sheet" as used herein will include any material wherein the present process is used to inspect or create a pore or plurality of pores. In certain embodiments, the sheet is presented as a section of a web of polymeric material or laminates of polymeric and/or other materials, such as metals. The sheet material may be hydrophobic and may include materials such as polycarbonates, polyimides, polyethers, polyetherimides, polyethylene and polyesters and the like. Other useful materials include non-polymeric, relatively rigid materials, such as metals, glasses or ceramics. For inspection applications the sheet may have the pores formed therein by any suitable method including LASER drilling or anisotropic etching through a thin film of metal or other suitable material. When used as a nozzle, e.g., for aerosol drug delivery, the sheet preferably has sufficient structural integrity so that it is maintained intact (will not rupture) when subjected to force in the amount up to about 40 bar, preferably of up to about 50 bar while the formulation is forced through the pores. In the preferred embodiment, the sheet is presented as a section of a web of polymeric material or laminates of polymeric and/or other materials, such as metals. However, the sheet is in general not limited to planar geometries. It would be obvious to one skilled in the art that the present invention may be applied to many geometries, metal parts used in fuel injection systems, or numerous other applications The term "pitch" as used herein generally refers to a sheet or multiplicity of sheets positioned in a single positioning operation for inspection and/or pore array fabrication. In the preferred embodiment, a pitch consists of an area or multiplicity of areas on a polymeric or laminate web. A pitch can include any number of sheets, but preferably includes from 1 to about 10 sheets, and more preferably includes from about 4 to about 8 sheets, and most preferably includes about 6 sheets.

The term "pore array" will be interpreted to mean any sheet having one or more holes therein. However, there are a number of types of preferred pore arrays which the system and method of the invention are particularly useful for producing and/or inspecting. Thus, the pore array may mean a sheet of material having any given outer parameter shape (may have a planar or a convex shape), wherein the sheet has one pore or a plurality of pores therein, which openings may be placed in a regular or irregular pattern, and which pores have an unflexed diameter of their exit aperture in the range of about 0.01 micron to about 100 microns and a pore density in the range from about 1 to about 1,000 pores per square millimeter for respiratory delivery. When the pore array is an array of nozzles for ocular delivery, the pores have an unflexed diameter of their exit aperture in the range from about 5 microns to about 50 microns, preferably from about 7.5 to about 25 microns, and a similar pore density. The nozzle array has a porosity of about 0.0001% to about 0.2%, preferably about 0.001% to about 0.1%. In one embodiment, the nozzle array comprises a single row of pores on, e.g., a large piece of sheet material. The pores may be cylinders perpendicular to the surface of the sheet, or may have a conical or other shape.

The terms "detector", "light detector" and the like are used interchangeably and will be interpreted herein to any device used to measure any property of incident light, including but not limited to energy, power, amplitude, phase, polarization, wavelength, beam width, radius of curvature, coherence, or propagation direction. Examples of detectors include imaging detectors such as CCD arrays, non-imaging detectors such as semi-conductor, bolometer, pyroelectric or thermoelectric detectors, or other device or material. Although it is preferable that the detector convert incident energy into electric current, it could also be possible to use mechanical means or other means of controlling process parameters based on properties of incident light.

General Overview

The invention provides a method of rapidly inspecting and analyzing multiple holes or through features present in a sample. The method comprises directing a light source producing a wavelength of light which is absorbed by the sample material, but which passes through the holes or through features and is detected by a light detector, for example a charge-coupled device. An imaging lens can be used to reduce the size of the image, thereby reducing analysis time and increasing throughput. This inspection method can be integrated into the manufacturing of pore arrays for a variety of uses.

FIG. 1 is a view of a schematic representation of the inspection system of the invention. The light source 1 is chosen based on a variety of criteria relating to factors such as how the wavelength of light emitted by the source will be effected by the material of the sheet 10 being inspected. Light from the source 1 may shine directly on the sheet 10 but is preferably directed through a light guide 2, e.g., optical fiber or optical fibers.

Light emitted from the light guide 2 may shine directly on the sheet 10 but is preferably directed through all or any of an optical diffuser 3, illuminated lens 4 and one or more spectral filters 5.

The light exiting the spectral filters 5 shines on the pore array 10. Substantially all if not all of the light striking the sheet is either absorbed or reflected and therefore does not travel through the sheet 10 unless the light enters one of the pores of the pore array. Light entering a pore is partially transmitted and strikes the light detector 8, which is preferably in the form of a charge-coupled device (CCD). Before contacting the light detector 8 the light may pass through an imaging lens 6 and an aperture stop 7. Once a pore array 10 has been inspected it is preferable to simply rotate a cylinder 11 containing new pore arrays and wind up the inspected pore arrays on the cylinder 12. In this manner one pore array after another can be inspected thereby providing an efficient inspection system.

All of the light exiting the pores of the pore array 10 is preferably contained within a light containment tube 13. This allows for an improved signal and also improves the stray light which might effect the signal on the light detector 8. After light has been detected on the light detector 8 the signal obtained is transmitted to a microprocessor 9 which carries out computer image analysis. The processing can be carried out in a variety of different ways and can focus on individual pores of the sheet or, more preferably, on the total signal received. If the total signal received is too small then the pores are insufficiently large, incorrectly shaped, or present in an insufficient pore density. If the signal received is too large than the pores are too large, are incorrectly shaped, or are present in an excessive pore density. Regardless of the criteria set once an analysis is made then the system provides a signal as to whether the pore array being inspected passes inspection or should be rejected.

System Components

The basic components of the system are shown in FIG. 1. However, of these components it is necessary to include the light source 1, detection means 8 and analyzing means 9. Analyzing means 9 is preferably a microprocessor, but could also be a discrete electronic controller, or a mechanical controller. The other components are preferably used in order to increase the accuracy and efficiency of the system. Most importantly, the system preferably includes a means for moving one or more sample sheets 10 after another into position for inspection or simultaneous fabrication and inspection. Each of the components as shown in FIG. 1 will now be described in further detail.

FIG. 5 shows the pore array 10 in place. The formulation 20 is in a container 21 and moves through a channel 22 to exit as an aerosol 23. This container 10 with the pore array 23 is disclosed within U.S. Pat No. 5,823,178.

The illumination light source 1 can be a commercially purchased light source sold under the trade name Ultracure 100SS Plus. The light source is a 100 watt mercury lamp system typically used in UV-curing applications. Mercury lamps typically emit strong spectral components at about 365 nm which is strongly absorbed by polyimide film having a thickness of 25 microns which film is sold by DuPont under the trade name Kapton. The light source does emit spectral peaks in the 300-400 nm range and has a useful spectral range of light of wavelengths less than 450 nm. The light having a wavelength of less than 450 nm is absorbed in the top few microns of the film which is 25 microns thick. Wavelengths longer than 550 nm are not absorbed at all but would be transmitted through the film. The combination of illumination and wavelength absorbed by the film determines the contrast between light transmitted through the film and light transmitted through the holes. Films can be used where all of the light is absorbed. Further, detectors can be used where wavelengths of light which pass through the film are not detected by the detector 8. The greater the contrast produced between light passing through the pores and light passing through the film, the more robust the image processing algorithms for image analysis.

Although essentially any type of light source can be used arc lamps are preferred and are characteristically small sources of light which enable more efficient focusing and collimation of the light. This makes it possible to transmit light into a light guide and also makes it possible to obtain relatively good collimation of the light emitted from the light guide. Collimated light on the inspection sample insures that the illuminated incident light is at the same angle for each hole in the film. If light were shown on the film at an angle this could provide distorted signals in that some signals entering the holes in the film at the beginning might not exit even though the hole was completely through the film. This would create an error which error would be enhanced as the film became thicker and/or the angle of the light increased. Other sources of light may clearly be used, so long as they are of a wavelength that can be transmitted through the desired pore, but are substantially blocked by the sheet.

A light guide such as the one sold under the trade name Lumatec may be used with the system of the present invention. Such a light guide has about a 5 mm core diameter and about a 1000 mm length. The light guide is selected due to its ability to transmit light of a wavelength in the range of about 300 to about 400 nm. The light guide assists in making the beam uniform at its exit face due to multiple bounces mixing rays within the fiber core guide region. The light guide ensures that the same amount of illuminating light is incident on each hole of the film. If a light source emits a uniform beam without a light guide the light guide could be eliminated. The mechanical flexibility and length of light guide provide additional degrees of freedom in order to address remote areas without the need for mirrors and relay lenses needed to obtain a free beam optical path. The light guide also makes it possible for the light source to be located at a distance away from the inspection area. This is a desirable feature although not a requirement.

It is also preferable to include an optical diffuser 3. The diffuser contributes to the uniformity of the beam on exiting the fiber. The diffuser consists of glass with gentle ripples on the surface on each side. Although the diffuser is not necessary some improvements in the accuracy of readings obtained could be expected by the use of a diffuser. A particularly preferred diffuser is the Coherent-Ealing glass diffuser.

The system also preferably includes an illuminating lens 4. A particularly preferred lens is sold under the name Melles-Griot which is a plano-convex, synthetic fused silica lens having a focal length of 25 mm. The lens collimates the beam coming from the light guide and directs the beam to the sample being inspected. It is also preferably to utilize spectral filters 5. Two spectral filters preferably used are sold under the trade name Schott Color Filter UG-11 and Schott Color Filter KG-3. This combination of spectral filters selects a 300 to 400 nm spectral band to be utilized for the inspection application for the holes on a Kapton film of the type described above. The UG-11 essentially blocks a visible portion and the KG-3 blocks the infrared portion resulting in UV being transmitted through the filtered combination. These transmission filters or a more suitable spectrally selected mirror could be an integral part of the illumination source precluding the need for external filters.

Different filters or combinations of filters can be used in order to block light that might be transmitted through the sheet even though a pore is not present. Accordingly, such a filter or group of filters could be placed at any desired position between the light source and detector including immediately in front of the light source (i.e., before the pore array) or immediately in front of the light detector. Provided the material of the sheet is comprised of material which is not transparent to any of the light then the filters are not necessary. However, when the sheet is particularly thin (as is often the case) and comprised of polymer materials (as is often the case) light is transmitted or at least some wavelengths of light are transmitted. Accordingly, to obtain accurate readings the filters are used to filter out the light that would be transmitted through the sheet even though a pore is not present.

Light passing through the pore array may pass directly onto the light detector 8. It is preferable that the light first pass through an imaging lens. A suitable imaging lens is sold under the trade name Melles-Griot symmetric-convex fused silica lens. This lens has a focal length of about 50 mm. The imaging lens focuses the light transmitted through the pore array to the detection element 8. The lens is not highly corrected for lens aberrations due to cost considerations. Custom lens designs could be utilized but would be more costly than commercially available lenses. Further, many of the different lens materials utilized in custom lens designs do not transmit ultraviolet light with high efficiency. Accordingly, simple and cost-effective solution was the selection of the simple single element lens which is held within the light containment tube 13.

After passing through the imaging lens 6 the light preferably passes through an aperture stop 7. A useful aperture stop is a variable iris sold by Thorlabs. The aperture stop is used to sharpen the resolution as needed. The smaller the aperture the greater the ability to reduce the effects of lens aberrations. Thus, the aperture is needed less if the lens includes no aberrations. By closing the aperture down it is possible to sharpen the image. This is especially useful for imaging lenses that are not corrected for off-axis rays such as the single element lenses described above.

After passing through the aperture 7 and the light contacts the light detection element 8. A useful light detector is sold by Sony and is a black and white CCD sold as model XC-75CE. The detection element is typically a standard charge-coupled device (CCD) of the type used in cameras which capture a two-dimensional image and allow computer image processing to be performed on the signal detected. A typical CCD is the type used in an eight-bit camera having 256 gray levels available per pixel. Cameras with greater or lesser than eight bits may also be used. A typical CCD chip in a camera has a size of about 4.8 mm vertically and about 6.4 mm horizontally containing 439,992 pixels. Each of the pixels is about 8.6 microns wide by about 8.3 microns vertically and there are 756 pixels horizontally and 582 pixels vertically. The configuration described here is a common CCD configuration used in cameras and provides a cost effective system. When the imaging lens is located for unity magnification: (1:1 imaging) the area which can be inspected is equal to the active area of the detection element. At this magnification it is possible to separate the bright spots in the image by a distance of approximately 5 pixels. If there are less than 5 pixels between bright spots the spots begin to blur together and the ability to correctly count the number of holes is compromised.

The information obtained from the detector 8 is forwarded to the microprocessor 9. A useful image acquisition and processing unit is Checkpoint 900C by Cognex. The frame grabber is a computer expansional electronics board which converts the image signal from the light detector 8 to a digital array of numbers consisting of gray levels and their pixel location in the two-dimensional image. This makes it possible for computer processing of the array of numbers (image processing). Blob analysis is a typical image-processing tool which is widely available commercially. This type of processing detects whether many bright pixels are adjacent to one another. Then the tool can count within the image the number of Blobs that are above a pre-specified threshold. The number of Blobs typically corresponds to the number of holes in the inspection sample. Another image processing tool which could be used is referred to as a "light meter" or "mean pixel value" which sums the gray levels of all of the pixels within a particular pre-specified region of interest (ROI) and calculates the average.

Simultaneous Manufacture And Analysis

The present invention is directed towards analysis of perforations in a material. In general, the method is used to scan a pore array which includes a plurality of pores and make an analysis as to whether or not the sheet passes or fails based on an analysis of a plurality of pores with consideration to a plurality of criteria simultaneously.

The invention is also designed so that pore arrays can be analyzed sequentially.

More specifically, the device for analyzing the sheets can include a means for holding the sheet in place while it is analyzed and a means for moving one sheet after another into an inspection position. This type of consecutive inspection/analysis procedure is useful during manufacturing. However, this method does not specifically affect the manufacturing other than to indicate that a sheet either passes or fails the inspection analysis.

In an alternative embodiment the invention can be designed so that it specifically affects, controls or improves the actual manufacturing/production process. Pore arrays made with currently known systems and techniques produce an average pore size that can vary unacceptably from pore array to pore array, or within a given pore array. For example, in pulmonary delivery of systemically active compounds, when an aerosol is created through a nozzle, the aerosol size is in general related to the size of the nozzle. Control of the pore size thus directly affects control of regional deposition in the lung. This alternative system and method are used to analyze each pore array as it is created and to provide feedback to adjust or stop the manufacturing/production process in order to reduce the variability of the size, shape, and or number of the pores. Because of this reduction in variability, smaller pores can also be reproducibly manufactured.

The basic components of such a closed-loop feedback system are schematically shown in FIG. 4 with the necessary components including an energy or LASER light source 20, an energy or light transport system 24, a detection means 28, and a feedback mechanism including an analyzing means 32 and feedback control lines 34 and/or 36. As mentioned above, the other components are preferably used in order to increase the accuracy and efficiency of the system. The system of FIG. 4 functions similarly to the system of FIG. 1 with the primary difference being that the light source 20 is used both for pore creation and inspection, and the additional use of a feedback control mechanism to adjust or discontinue the pore array manufacturing process (e.g., the delivery of light to the sheet, the position of the pore array, the temperature, etc.).

The LASER light from energy source 20 may be delivered through an optional light guide 22, e.g., optical fiber or optical fibers and is preferably directed through an energy or light transport mechanism 24 positioned prior to the sheet (on the entry side of the sheet) which finely focuses the LASER light to drill or form pores or holes within sheet 38. The light transport mechanism may comprise a shutter, homogenizer, mask, and/or projection lens, an optical system well suited to the use of excimer LASERs. Suitable projection lenses would have a large field of view, from about 2 mm to about 60 mm, preferably from about 5 mm to 45 mms, still more preferably from about 25 to about 40 mm. The effective focal length would generally range from about 100 to about 500 mm, preferably from about 150 to about 350 mm, more preferably from about 200 to about 300 mm. The Numerical Aperture ranges from 0.04 to about 2, preferably from about 0.005 to about 1.5, more preferably from about 0.75 to about 1.25. The projection lens is usually a 2× to 10× reduction, preferably 3× to 7× reduction and more preferably about a 5× reduction. The shutter is in general a mechanical means for shutting off the beam and in general needs to stop the beam rapidly, in approximately 2 to about 25 ms, preferably from about 4 to about 15 ms, more preferably in about 8 ms. These actuation times can be achieved in many ways, including motors, pneumatics, acousto-optics, and the like, but in the preferred embodiment employ solenoids. Alternatively, the light transport mechanism may comprise an optional spatial filter, an optional diffractive element, and a focusing lens, an optical system better suited to LASERs such as frequency multiplied Yittrium-Aluminum-Garnet (YAG) or similar LASERs. The LASER light may be transmitted in a continuous stream or as discrete pulses depending on the desired result. Upon formation of a pore, light passes through the pore and is transmitted to and strikes light detector 28 which is positioned on the opposite side or exit side of sheet 38. As with the system of FIG. 1 before contacting light detector 28, the light may pass through an imaging lens 26 and an aperture stop 27. Alternatively, the transmitted light may simply fall directly on the detector, in the cases where only the total transmitted power is measured, or when the detector is close enough to the pore array that the light from individual pores is distinguishable. All of the light exiting the pores of the pore array 28 is preferably contained within a light containment structure 30 in order to minimize light from straying which might affect the signal on the light detector 28. After light detector 28 detects the light, a signal representative of one or more parameter of the LASER light, e.g., temporal and/or spatial distributions of the light's power or intensity level, is transmitted to a feedback control 32 which carries out analysis of one or more parameters known to be affected by pore size, shape, or density. Based on this analysis, and in particular, based on the determination as to whether the light parameter is below or above a certain threshold level, a control signal is sent from feedback control 32 back to LASER light source 20 and/or to energy transport system 24 and/or to tape transport 42 via signal lines 34, 36, and/or 43, respectively. Pore size may be controlled where the threshold level corresponds to the optimum pore size. The control signal may be used to turn the energy source 20 on and off or to adjust the energy transport system, e.g., vary the power of a continuous light beam or vary the frequency of pulsed light. For example, where LASER light is provided in a single, continuous pulse, the control signal may involve discontinuing the pulse. Where the LASER light is provided in a series of discrete pulses, the control signal may involve reducing the number, duration, or frequency of pulses. Reducing the number of pulses to zero, or ending a continuous pulse, may be achieved by controlling the LASER, or with and external shutter. In addition, if the analysis determines that the pore array fails some criterion that cannot be fixed with further processing, e.g., the pores are too large, then the sheet may be marked, removed, or otherwise identified as flawed. Once pores have been satisfactorily formed within a sheet 38, multiple sheets 38, or a section of sheet 38, the sheet maybe advanced from a formation/inspection position to allow for formation of additional pores in another sheet, series of sheets, or in another section of the same sheet.

Energy source 20 is preferably a LASER light such as a UV LASER, an IR LASER or a visible light LASER.

Examples of UV LASERs that are suitable for use with the present invention include a Nd:YAG or Nd:YLF frequency multiplied UV LASER, preferably a solid state diode pumped Nd:YAG frequency tripled LASER with 2-20 nanosecond pulses emitting light at 355 nanometers LASER. Preferably the LASER is an excimer LASER, with a wavelenght from about 100 to about 500 nm, preferably from about 193 to about 350 nm, most preferably from about 248 or about 308 nm. The prefered chemsities of the excimer LASER are xenon/chlorine or krypton/florine. The excimer systems are generally pulsed, with repetition rates of about 50 to about 1000 hz, preferably from about 100 to about 400 hz, and most preferably about 300 Hz. An example of a suitable LASER is the Lambda Physik Steel 1000 LASER, although it will be obvious to one skilled in the art that other LASER systems could be used. Pulse durations are generally in the range of from about 10 to about 100 ns, preferably from about 15 to about 40 ns, and most preferably about 28 ns. Pulse energies will vary based on the application, but will be generally in the range of about 1 mJ to about 1000 mJ, and for the fabrication of pore arrays in thin polymer films they will be preferably from about 300 to about 800 mJ, most preferably from about 400 to about 600 mJ. The pulse energy incident on the sheet will range from about 0.01 mJ to about 10 mJ, for the fabrication of pore arrays in thin polymer films they will be preferably from about 3 to about 8 mJ, most preferably 4 to 6 mj. A suitable IR LASER for use with the present invention is a short (1-100 femtosecond) pulse IR. It would be obvious to those skilled in the art to substitute other light sources and frequency mutliplying schemes as appropriate for the process and materials under consideration Energy transport system 24 may be a lens system which may include one or more means for creating one or more focused beams of light characterized by parameters for the size and shape of the one or more pores or spots to be formed. Such means may include but are not limited to one or more of the following: a beam-expander, a final objective/projection lens, a spatial filter, a variable attenuator, a beam splitter for directing energy at multiple locations at once, or a galvo mirror for rapidly directly energy to multiple locations simultaneously. The beam splitter may be based on refraction/transmission interfaces or on diffractive optics, or can be split using a homogenizer. Various types of diffractive optic beam splitters may be used including but not limited to those based on a transmission mask, on phase difference optics or on index of refraction, or a combination thereof, each of which may be either binary, stepped, or continuously varying. The beam splitter may divide the beam in one or two directions, providing a few beams (about 4 or more) or a large array of dozens or hundreds of beams. The beam splitter may produce a 1-dimensional array of about 4 to about 100 beams, for example, or a two-dimensional array of about 12 to about 1000 beams, for example, or multiple copies of the above arrays.

Where multiple pores are being formed, the parameters of the energy directed by energy transporter 24 may be the same and controlled in the same way for all of the pores or spots, or may be different and controlled differently from pore to pore or from spot to spot. The power or intensity (both temporal and spatial distribution) of the delivered energy may be preset such that in one or more regions of the material to be drilled it is above or below a threshold level, such as for example, the threshold for damage to the material, the threshold for thermal ablation of the material, or the threshold for photoablation of the material. For many applications, it may be preferable to initially select a power intensity level that produces holes that are smaller than desired but which can be adjusted as needed to achieve the optimal size. In this way, the risk of forming holes which are too large is minimized and the cost of rejecting damaged or useless material is reduced. The total amount of energy per pore may vary from application to application. Typical ranges for micro-meter scale structures fabricated using pulsed UV LASERs suitable for, for example, aerosol drug delivery nozzles in thin polymer films include from about 0.1 to about 5 microjoules per pulse, more typically from about 0.2 to about 1 microjoule per pulse, and even more typically from about 0.2 to about 0.6 microjoule per pulse. The transmitted energy per pulse per pore at the end of the fabrication process will in general also vary from application to application, depending on for example the size and shape of the pore, the properties of the light source, and the material of the sheet. Typical ranges for micro-meter scale structures fabricated using pulsed UV LASERs suitable for, for example, aerosol drug delivery nozzles in thin polymer films include from about 1 femtoJoule to about 1 microjoule per pulse, from about 1 femtoJoule to about 1 nanojoule, or from about 10 femtoJoule to about 20 picoJoule. The energy density per spot per pore using pulsed UV LASERs in a polymeric material like polyimide may range from about 0.1 to about 2 Joules/$cm^2$ (1 to 20 nJoule per square micrometer), or more typically from about 0.25 to about 0.4 Joules/$cm^2$ (2.5 to 4 nJoule per square micrometer). As mentioned above, the energy may be delivered continuously or in pulses. If in pulses, the pulses may have any suitable duration, for example, from about 1 to about 100 nanoseconds, or less than about 1 nanosecond, or less than about 1 picosecond.

Detector means 28 which measures some property of the light transmitted through the formed hole or holes may comprise a single detector configured to detect the energy passing through some or all of the holes, or may comprise two or more sub-detectors, each configured to detect energy from less than all of the holes. Detector means 28 may include but is not limited to a semi-conductor, bolometer, pyroelectric detector, thermoelectric detector, down-conversion/photodiode, or other device or material that converts incident energy into electric current. An example of a suitable detector for detecting transmitted power is a HUV-4000B operational amplifier photodiode combination (EG&G Optoelectronics). Another example of a suitable detector for detecting transmitted power is a Star Tech downconversion/photodiode Energy Detector, model number XR-16-G. In a preferred embodiment, the beam from the LASER is directed toward multiple areas on the sheet, each area being a target for the fabrication of an individual nozzle array. Individual target areas each have their own detector, and each detector is used to cut off the power to each target area using a shutter. Detector means 28 may also be a photo-diode or charge-coupled (CCD) device. Detector 28 may include an optical input filter which is configured to pass the particular drilling wavelengths of the LASER light and to reject other wavelengths, thus increasing the sensitivity of the detector by eliminating background light. The time constant of the detector 28 or the time constant of the electrical output of the detector 28 may be such that it allows measurement of individual pulse energy, measurement of the temporal shape of the individual pulses or the weighted integral of the energy of multiple pulses, or a combination thereof. The detector 28 may also implement phase-sensitive detection, such as a lock-in amplifier circuit referenced to the pulses of the LASER. The output of detector 28 may be further filtered to improve signal quality.

The feedback control mechanism uses the output of detector 28 to determine whether the light being delivered to the pore sites requires adjustment or if a new sheet or sheets should be moved to the processing position. In the case of multiple pore sites, this determination may include identifying which of the pore sites require adjustment and which do not. The feedback control or adjustment may be achieved by sending a control signal via signal line 34 to, for example, turn off the energy source 20 such as when the transmitted energy rises above a threshold level which indicates that the desired hole size has been achieved for a particular pore site or set of pore sites. For example, the LASER power may be adjusted or stopped completely when the detector measures an incident power. Alternatively, a control signal sent via signal line 36 may be used to adjust the energy delivery system 24 in order to modify or interrupt the delivery of energy to one or more array sites while the energy delivered to other array sites is maintained until their respective pores achieve the target configuration, e.g., size. One means for accomplishing this is to provide as a part of the energy delivery system 24 a shutter for each beam or set of beams of LASER light impinging on the sheet or for each pore site. The shutter may be positioned anywhere between the light source and the sheet to be drilled, but must be down stream of any beam splitting component if individual beams or series of beams are to be shut off individually. When some parameter of the transmitted light, preferably the target energy level of the LASER light (i.e., the level corresponding to the desired pore size) passing through the sheet at a particular pore site or set of pore sites is achieved, the feedback mechanism triggers the shutter to block that particular beam, thereby preventing further drilling of the sheet and enlargement of the hole or holes. Another way of accomplishing this is by using an adjustable beam attenuator. Yet another way of accomplishing this is to signal the tape transport mechanism to move to the next sheet or set of sheets to begin drilling there.

The feedback system may use integrated and filtered outputs from the detector 28 to determine the appropriate action based on the accumulated transmitted energy of one, a few, or all pulses used in the drilling operation. This determination may include averaging the energy of some or all pore sites either with equal or unequal weighting.

The determination may use exponential weighting as occurs when the detector time constant is similar to the pulse repetition rate. The feedback system may be used, after the determined amount of transmitted energy is measured, to change some parameter of the process until a different transmitted energy level is achieved, or until a certain number of additional pulses are delivered, or until some other action is accomplished or criterion is achieved. The various parameters which may be controlled include but are not limited to the intensity or power of the delivered energy, the pulse rate, the fluence, the focal point of the LASER, the pulse duration, and/or the pulse repetition rate The pores to be formed using the present invention can have any size and shape. For aerosolization nozzles, they have dimensions ranging from about 0.1 to about 50 micrometers, preferably about 0.3 to 10 micrometers. For pulmonary drug delivery, the pores will in general range from about 0.1 micrometer to about 10 micrometer, preferably from about 0.3 micrometer to about 2.5 micrometer, more preferably from about 0.4 micrometer to about 1.4 micrometer. The pores can have any shape, including roughly conical shapes, cylindrical shapes, or combinations thereof. The exit of the pore can have any shape, but is preferably approximately circular.

The beams delivered to the sheet may have any radial shape including but not limited to substantially circular and may be characterized by any appropriate profile including but not limited to roughly gaussian or top-hat profiles. Any suitable number of pores or holes may be formed including from one hole to several hundreds or more.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

This experiment demonstrates the use of a method of the invention to inspect holes in a sample. A mercury arc lamp of the type commonly used for ultraviolet adhesive curing was used for the light source. The ultraviolet portion of the spectrum was specifically isolated between about 300 and 400 nanometers utilizing appropriate reflective and transmissive optical filter elements well known to those skilled in the art. This ultraviolet portion consisted mainly of the strong emission line from mercury at 365 nanometers. The filtered light was guided via a commonly used liquid light guide which transmits near ultraviolet in the spectral range selected. At the output of the fiber, a diffuse reflectance glass was used to provide additional homogenization of the beam exiting the guide. A condensing lens was then used to collimate the light and illuminate the sample to be inspected. The sample was a polyimide film. Spectral filters were located in the collimated light to ensure the rejection of any detectable visible and infrared light which would transmit through the sample substrate. An imaging lens was positioned in back of the sample to provide an image onto a light detection element. This element was a charge-coupled device or CCD. In close proximity to the imaging lens was an aperture stop which, when closed down to a small diameter, produced a clearer image at the CCD. The image was displayed on a monitor and the image information stored into a computer image file. This image was processed in order to determine the number and size of features in the sample. For example, a nozzle with an array of hundreds of through holes appeared on the image as an array of bright spots. The number of spots in the image should correspond exactly to the number of holes designed into the part. The amount of light incident on the CCD from each hole is transformed into gray levels covering picture elements or pixels in the CCD. These gray levels ranged from 0 to 255 for 8-bit CCD cameras. The pixels corresponding to each hole were defined as a cell, and the sum of the pixel gray levels within each cell was determined and correlated with the size of the hole. Thus image processing enabled the determination of both the number and size of the holes in the array.

Example 2

This experiment demonstrates the use of a method of the invention to inspect holes in a sample. A mercury arc lamp of the type commonly used for ultraviolet adhesive curing was used for the light source. The ultraviolet portion of the spectrum was specifically isolated between about 300 and 400 nanometers utilizing appropriate reflective and transmissive optical filter elements well known to those skilled in the art. This ultraviolet portion consisted mainly of the strong emission line from mercury at 365 nanometers. The filtered light was guided via a commonly used liquid light guide which transmits near ultraviolet in the spectral range selected. At the output of the fiber, a diffuse reflectance glass was used to provide additional homogenization of the beam exiting the guide. A condensing lens was then used to collimate the light and illuminate the sample to be inspected. The sample was a polyimide film. Spectral filters were located in the collimated light to ensure the rejection of any detectable visible and infrared light which would transmit through the sample substrate. An imaging lens was positioned in back of the sample to provide an image onto a light detection element. This element was a charge-coupled device or CCD. In close proximity to the imaging lens was an aperture stop which, when closed down to a small diameter, produced a clearer image at the CCD. The image was displayed on a monitor and the image information stored into a computer image file. This image was processed in order to determine the number and size of features in the sample. For example, a nozzle with an array of hundreds of through holes appeared on the image as an array of bright spots. The number of spots in the image should correspond exactly to the number of holes designed into the part. The amount of light incident on the CCD from each hole is transformed into gray levels covering picture elements or pixels in the CCD. These gray levels ranged from 0 to 255 for 8-bit CCD cameras. A region of interest encompassing an entire array of holes is identified. The light meter tool is used to determine the average light level transmitted by the array of holes. This light level corresponds to an average calibrated hole size for the array.

Example 3

This experiment demonstrates the use of a method of the invention to form and inspect spots in a 25 micrometer thick polyimide sheet. The energy source used was a frequency tripled niobium yttrium based LASER emitting 355 nm wavelength pulses, each having approximately 0.4 to about 0.6 microjoule of energy. The LASER was focused on spot having a diameter of about 12 to about 15 micrometer and produced a hole with an exit diameter between about 0.4 and about 0.6 micrometer. The formed hole passed approximately 0.5 to about 10 picojoules which was detected by a silicone diode detector. Based on the signal from the detector, a discrete electronic feedback circuit comprising a comparator, a reference voltage and logic gates sent an electronic signal to the LASER to stop generating light pulses.

Several sets of pore arrays were fabricated using the same light source and optical system drilling one pore at a time. Some arrays were produced using a predetermined number of pulses and some using the feedback system to control the number of pulses used to drill in an attempt to control the size of pores produced. The following data illustrate the improvement in control of pore size that was achieved by the implementation of feedback. Each value in "Array Avg. Size" is the average size of ten pores within a single array, and "SD, Intra" gives the standard deviation of these ten pore sizes for each of the arrays. "SD, Inter" is the standard deviation of the "Array Avg. Sizes" values within a session, and the "Session Avg. Size" is their average. The pore size within each nozzle is better controlled, the average pore size of each pore array during fabrication session is better controlled, and the average pore size of all arrays in a given session is closer to the targeted size, 595 nm in these cases. All sizes are given in nanometers.

| Array # | Array Average Size (nm) | SD Intra |
|---|---|---|
| Fabrication Session without Feedback | | |
| 1 | 550 | 20 |
| 2 | 613 | 76 |
| 3 | 631 | 20 |
| 4 | 631 | 99 |
| 5 | 603 | 61 |
| 6 | 586 | 36 |
| 7 | 617 | 33 |
| 8 | 589 | 52 |
| 9 | 672 | 75 |
| Session Average Size | 610 | |
| SD Inter | | 34 |
| Fabrication Session with Feedback | | |
| 1 | 597 | 9 |
| 2 | 583 | 10 |
| 3 | 589 | 12 |
| 4 | 590 | 18 |
| 5 | 598 | 13 |
| 6 | 598 | 15 |
| 7 | 609 | 14 |
| 8 | 594 | 12 |
| 9 | 599 | 14 |
| 10 | 600 | 9 |
| 11 | 592 | 26 |
| Session Average Size | 595 | |
| SD Inter | | 7 |
| Fabrication Session with Feedback | | |
| 1 | 603 | 16 |
| 2 | 590 | 9 |
| 3 | 602 | 14 |
| 4 | 591 | 9 |
| 5 | 586 | 11 |
| 6 | 597 | 9 |
| 7 | 578 | 13 |
| 8 | 602 | 16 |
| 9 | 592 | 12 |
| 10 | 586 | 16 |
| 11 | 595 | 14 |
| Session Average Size | 593 | |
| SD Inter | | 8 |

Example 4

This experiment compares the average pore sizes of micron-size pores formed within a sheet or nozzle by means of a closed-loop feedback system of the present invention and a prior art open-loop system. The system used was an Excimer LASER with a wavelength of 308 nm. The optics system was a projection system, that simultaneously fabricated 6 separate pore arrays. The beam from the LASER was split at the homogenizer, and each beam had its own mechanical shutter. The shutters were designed specifically for this application, and were actuated using solenoids. Below each of the 6 sheets were 6 separate Star Tech XR-16-G Detectors. When the power measured by a detector exceeded a predetermined threshold, the shutter for that beam was closed. When all 6 pore arrays were fabricated, a new set of 6 sheets were moved into position, and the process was repeated. Under the ablation stage there were six lenses that relayed the laser energy coming through the sheet (25 micro-meter thick polyimide film) onto six Star Tech sensors, these lenses were set at a 1 to 1 magnification with a focal plane about 2 mm above the sensors. There was also an attenuator plate above the sensors to cut the intensity into all the sensors.

Ten nozzle arrays were fabricated using a closed-loop drilling method (CL) and ten were fabricated using a similar open loop drilling Method (OL). For each time the sheets were positioned in the drilling area (1 "pitch"), 6 nozzles or sheets (N1-N6) were drilled with each nozzle array having an average of about 15 holes. For each drilling application, the following values are provided: average hole size (microns) per nozzle array, the standard deviation between nozzle array hole size averages for each pitch (PSD) and the standard deviation of nozzle hole size averages from pitch to pitch (P/PSD). The standard deviation between nozzle averages for each pitch (PSD) undergoing a closed-loop drilling application was significantly lower than for open-loop drilling applications. This is most dramatically demonstrated when comparing the pitch-to-pitch standard deviation P/PSD) for the closed-loop drilling applications (PSD=0.04 micrometers) with those of the open-loop drilling applications (PSD=0.17 micrometers). Similar results were found when performing a similar experiment for the formation of sub-micron size pores.

| Pitch | N1 | N2 | N3 | N4 | N5 | N6 | PSD |
|---|---|---|---|---|---|---|---|
| Closed-Loop Application (all units are micrometers) | | | | | | | |
| CL1 | 1.39 | 1.61 | 1.39 | 1.53 | 1.35 | 1.44 | 0.10 |
| CL2 | 1.43 | 1.66 | 1.37 | 1.73 | 1.41 | 1.47 | 0.15 |
| CL3 | 1.44 | 1.37 | 1.37 | 1.51 | 1.33 | 1.40 | 0.06 |
| CL4 | 1.28 | 1.35 | 1.39 | 1.41 | 1.43 | 1.28 | 0.07 |
| CL5 | 1.27 | 1.64 | 1.38 | 1.47 | 1.51 | 1.44 | 0.12 |
| CL6 | 1.49 | 1.39 | 1.44 | 1.42 | 1.34 | 1.39 | 0.05 |
| CL7 | 1.41 | 1.60 | 1.24 | 1.55 | 1.42 | 1.40 | 0.13 |
| CL8 | 1.29 | 1.50 | 1.48 | 1.49 | 1.33 | 1.41 | 0.09 |
| CL9 | 1.45 | 1.45 | 1.35 | 1.50 | 1.42 | 1.38 | 0.05 |
| CL10 | 1.41 | 1.49 | 1.36 | 1.60 | 1.43 | 1.57 | 0.09 |
| P/PSD | | | | | | | 0.04 |
| Open-Loop Application (all units are micrometers) | | | | | | | |
| OL1 | 1.60 | 1.36 | 1.66 | 1.49 | 1.84 | 1.70 | 0.17 |
| OL2 | 1.63 | 1.38 | 1.67 | 1.56 | 1.70 | 1.50 | 0.12 |
| OL3 | 1.97 | 1.73 | 2.04 | 1.90 | 2.15 | 1.96 | 0.14 |
| OL4 | 1.64 | 1.43 | 1.64 | 1.53 | 1.95 | 1.66 | 0.18 |
| OL5 | 1.60 | 1.39 | 1.74 | 1.51 | 1.69 | 1.64 | 0.13 |
| OL6 | 1.94 | 1.74 | 1.99 | 2.00 | 2.22 | 2.07 | 0.16 |
| OL7 | 1.90 | 1.59 | 1.94 | 1.67 | 1.98 | 1.90 | 0.16 |
| OL8 | 1.54 | 1.36 | 1.87 | 1.69 | 1.94 | 1.85 | 0.22 |
| OL9 | 1.37 | 1.32 | 1.58 | 1.29 | 1.77 | 1.65 | 0.20 |
| OL10 | 1.67 | 1.46 | 1.75 | 1.64 | 1.95 | 1.63 | 0.16 |
| P/PSD | | | | | | | 0.17 |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method, comprising:

directing light onto a polymer film, the light having an intensity and a wavelength sufficient to form a plurality pores within the sheet;

forming a pore array within the sheet comprising a plurality of pores at locations where the light contacts a surface of the sheet, wherein the light passes through the plurality of pores;

detecting the light passing through the plurality of pores;

analyzing the detected light to determine if the plurality of pores meet a pore size and pore shape criterion; and moving formulation through the pores to create an aerosol.

2. The method of claim 1, further comprising:

inhaling the aerosol into lungs of a patient.

3. The method of claim 1, further comprising:

modifying the method based on whether the pore size and pore shape criterion is met.

4. The method of claim 1, wherein the light is a LASER.

5. The method of claim 1, further comprising:

repeating the directing, forming, detecting, and analyzing for each of a plurality of sheets.

6. The method of claim 1, wherein each of the plurality of pores formed has a diameter of less than about 100 microns.

7. The method of claim 4, wherein the LASER is selected from the group consisting of a UV LASER and a visible light LASER.

8. The method of claim 1, wherein the detecting comprises using a detector selected from the group consisting of a photodiode, a pyroelectric detector and a downconversion/photodiode, and wherein the analyzing comprises using a system comprising an electronic circuit.

9. The method of claim 3, wherein the modifying comprises changing one or more of the intensity, the pulse duration, and the pulse frequency of the directed light.

10. The method of claim 9, wherein the modifying comprises reducing the intensity wherein the fabrication method is essentially halted.

11. The method of claim 3, wherein the modifying comprises moving a new sheet into the drilling position.

12. The method of claim 7, wherein the UV LASER is selected from the group consisting of excimer LASERs, frequency multiplied YAG LASERs, frequency multiplied YLF LASERs.

13. The method of claim 4, wherein the LASER is a pulsed Excimer LASER.

* * * * *